United States Patent [19]
Gleaves

[11] Patent Number: 6,087,180
[45] Date of Patent: *Jul. 11, 2000

[54] METHOD FOR STUDY AND ANALYSIS OF PRODUCTS OF CATALYTIC REACTION

[76] Inventor: John T. Gleaves, 225 Urbauer Hall, St. Louis, Mo. 63130

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/738,571

[22] Filed: Oct. 28, 1996

Related U.S. Application Data

[63] Continuation of application No. 08/580,756, Dec. 29, 1995, abandoned, which is a continuation of application No. 08/332,344, Oct. 31, 1994, Pat. No. 5,500,371, which is a division of application No. 08/056,124, Apr. 30, 1993, Pat. No. 5,376,335.

[51] Int. Cl.$^7$ ............................................. G01N 31/10
[52] U.S. Cl. ........................ 436/37; 436/159; 436/161; 436/173; 250/282
[58] Field of Search ..................... 436/37, 52, 159, 436/161, 173; 250/282, 288

[56] References Cited

U.S. PATENT DOCUMENTS

| | | | |
|---|---|---|---|
| 3,431,077 | 3/1969 | Danforth | 436/37 |
| 3,943,363 | 3/1976 | Amblard | 250/288 |
| 4,045,359 | 8/1977 | Fletcher et al. | 422/186 |
| 4,626,412 | 12/1986 | Ebner et al. | 422/50 |
| 4,663,297 | 5/1987 | Yates, Jr. et al. | 436/37 |
| 5,009,849 | 4/1991 | Ebner et al. | 422/83 |
| 5,039,489 | 8/1991 | Gleaves et al. | 422/68.1 |
| 5,047,212 | 9/1991 | Blades et al. | 422/82.02 |
| 5,120,315 | 6/1992 | Hessel | 604/132 |
| 5,132,472 | 7/1992 | Durante et al. | 568/910 |
| 5,264,183 | 11/1993 | Ebner et al. | 422/83 |
| 5,376,335 | 12/1994 | Gleaves | 422/80 |
| 5,500,371 | 3/1996 | Gleaves | 436/37 |

Primary Examiner—Lyle A. Alexander
Attorney, Agent, or Firm—Senniger, Powers, Leavitt & Roedel

[57] ABSTRACT

Apparatus and process for real time analysis of the intermediates and products of a gas phase chemical reaction catalyzed by a particulate catalyst. Real time analysis is conducted under high vacuum using a detection device contained within a high vacuum chamber. The reactor is connected to the vacuum chamber but is outside thereof, allowing the reactor to be operated either at high vacuum or under moderate pressure. Reactors and reactor feed manifolds of varying configuration may be interchangeably connected to the vacuum chamber on an essentially modular basis. Only a single vacuum system is required for the apparatus. Reaction products may also be analyzed by methods such as gas chromatography. Simultaneously with real time analysis of reaction products and intermediates, infrared, ultraviolet other reflected electromagnetic analyses may be conducted on the reacting gases or catalyst surface.

7 Claims, 2 Drawing Sheets

METHOD FOR STUDY AND ANALYSIS OF PRODUCTS OF CATALYTIC REACTION

This is a continuation, of application Ser. No. 08/580,756, filed Dec. 29, 1995, now abandoned which is a continuation of application Ser. No. 08/332,344, filed Oct. 31, 1994, now U.S. Pat. No. 5,500,371, which is a divisional of application Ser. No. 08/056,124, filed Apr. 30, 1993, now U.S. Pat. No. 5,376,335.

BACKGROUND OF THE INVENTION

This invention relates to conducting and studying catalysis and catalyzed chemical reactions particularly heterogenesis catalytic reactions.

Development of new catalysts in catalyzed reactions has been hampered by the difficulty encountered in obtaining basic information about the physical and chemical processes involved in catalytic activity and catalytic reactions, such as reaction intermediates, reaction mechanisms, adsorption, and desorption of reactants and products in catalytic reactions, oxidation and reduction of catalysts, catalyst poisons, the concentration of reactants on a catalyst surface, and others.

Classically, this kind of basic information about the chemical and physical processes of catalysis has been deduced primarily from analysis of the final product of the reaction. Conclusions have been based on final products because of the difficulty in isolating and analyzing reaction intermediates, many of which are highly fragile in reactive species. Being able to determine directly the identity of these intermediates and to follow their production and consumption during the reaction would increase the understanding of catalysis and would facilitate the development of catalysts and catalytic processes.

One method that has been used to study the interaction of catalytic surfaces with reactant molecules is called molecular beam mass spectrometry. In this technique, a stream of molecules of reactant gas (a molecular beam) is directed at a target of the catalytic material, with the target oriented at an angle to the molecular beam. The molecules of the reactant gas strike the target, some of them react to form products and intermediates, and they rebound off the target in the direction of an aperture. A portion of the rebounding molecules pass through the aperture into the ionization chamber of a mass spectrometer, which analyzes the mixture for reactants, intermediates, and products.

A variation on this molecular beam technique is called modulated molecular beam mass spectrometry, in which the initial molecular beam of reactant gas is modulated, such as with a rotating "chopper", to produce a series of pulses of the reactant gas. The result is that a series of pulses of gas enter the mass spectrometer for analysis.

In these molecular beam techniques, the entire assembly is enclosed and is operated in a vacuum. The vacuum is necessary to achieve the molecular flow to form the molecular beam, and is necessary for operation of the mass spectrometer.

The vacuum required, along with the fact that the molecules strike the catalyst target and rebound to the detector combine to make the number of reaction opportunities for each molecule of reactant very small. It has been estimated that the number of collisions between a given molecule of reactant gas and the target catalyst would be 10 or less, and that the number of collisions between a given molecule of reactant gas and other gas molecules would also be 10 or less. This means that these molecular beam techniques are practical only for highly reactive systems, in which sufficient reaction occurs in the small number of reaction opportunities to produce detectable amounts of products and intermediates. Most commercially important catalyzed reaction systems are not reactive enough for use with molecular beam techniques. The catalyst suitable for use with molecular beam techniques must be made into a target with a surface regular enough so that the direction of rebound of the reactant gas molecules can be directed toward the mass spectrometer. Not all catalysts can be formed into such a target.

Conventional techniques have been adapted to try to isolate and analyze for reaction intermediates. One common technique involves a reactor containing a catalyst, through which an inert carrier gas flows continuously. A pulse of reactant gas is injected into the carrier gas and is carried through the catalyst. As the product gas exits the reactor, samples are taken and analyzed. This type of system is normally operated at or near atmospheric pressure. The number of collisions between an average molecule of reactant gas and the catalyst is very high, and has been estimated to be far greater than $10^6$. Similarly, the number of collisions between an average molecule of reactant gas and other gas molecules has been estimated to be far greater than $10^6$. Due to the large number of reaction opportunities, the number of fragile and highly reactive intermediates that emerge from the catalyst is very small, and is usually too small to be detected.

U.S. Pat. Nos. 4,626,412 and 5,009,849 describe a system and process for temporal analysis of the products of catalyzed chemical reactions. The temporal analysis of product system ("TAPS") described in these patents comprises an enclosed housing containing a catalytic reactor, a pulse generator for introducing a pulse of reactant gas into the reactor and for withdrawing a pulse of product gas from the reactor, a collimating slit for producing a resolved pulse of product gas in which the molecules of the product gas move in substantially parallel paths, and a quadrupole for mass spectrometry or other means for providing real time analysis of the resolved pulse product gas. A clock senses the pulse of reactant gas introduced into the reactor by a pulse generator and activates a signal averager that is in communication with the mass spectrometer to receive a signal for a designated period of time and store it. The signal averager stores the signals from a series of pulses and averages them to reduce noise.

The catalytic reactor of the '412 and '849 patents typically contains a particulate catalyst in a physical form comparable to that which would be used in a commercial catalytic reactor. The amount and surface area of the catalyst is sufficient for conversion of reactants to intermediates and products, even in cases where the reaction rate is relatively slow. The collimating slit establishes a beam of reaction product from the product pulse exiting the reactor which is then analyzed in real time by the mass spectrometer.

The TAPS system disclosed in the aforesaid '412 and '849 is operated under high vacuum. Both the reactor and product gas analytical detector are contained within a high vacuum chamber. This chamber is divided into three compartments, the first of which contains the reactor and collimating slit, the second contains a cryogenic trap, and the third contains the quadrupole. A separate vacuum pump is provided for each of the three compartments. In the system of the '412 and '849 patents, operation in both the analytic detection region and the catalytic reactor is conducted under high vacuum.

U.S. Pat. No. 5,039,489 also describes an apparatus for catalyst analysis in which both the catalytic reactor and quadrupole detector of a mass spectrometer are contained within a single vacuum chamber. Alternatively, the '489 patent describes operating the reactor under pressure while the product gas is divided between a stream that is reduced in pressure and subjected to mass spectrometric analysis and another stream which is analyzed on a gas chromatograph. Pressure in the reactor is controlled by a back pressure regulator in parallel with the gas chromatograph. Product gas flowing from the reaction chamber into the vacuum chamber for mass spectrometric analysis passes through a fine orifice in which the pressure of the reaction gas is reduced from the pressure maintained in the reactor to the high vacuum required for analysis of the gas product.

Since prior art methods which apply surface science techniques to the study of catalysts and catalytic reactions have essentially all required that analytical observations be made under very high vacuums, a problem is presented in extrapolating the data to predict effects at the operating pressures of commercial catalytic reactions, nearly all of which are conducted at pressures above 100 torr. The pressure difference, which extends over a number of orders of magnitude, typically has effects on reaction kinetics, absorption and desorption phenomena and the like which compromise the value of observations taken at very high vacuum. This problem, commonly referred to in the literature as the "pressure gap," has inhibited progress in understanding catalytic reactions, and consequently the development of technology for such reactions.

SUMMARY OF THE INVENTION

Among the several objects of the present invention may be noted the provision of a system and process for analysis of the products of a catalytic chemical reaction; the provision of such system and process by which rates and mechanisms of a catalytic reaction may be studied; the provision of such system and process by which intermediates can be identified, and the mechanisms and rates of formation and consumption of such intermediates studied; the provision of such system and process by which catalyst structures and mechanisms of operation may be studied; the provision of such system and process by which catalytic reactions may be studied either under high vacuum or at ambient and above ambient pressures; the provision of such system and process by which reaction products, intermediates and catalysts may be studied by a variety of analytical techniques; and the provision of such system and process by which a particular catalyst may be studied using the same reactor for real time analysis of intermediates and by simulation of commercial operation.

Briefly, therefore, the present invention is directed to an apparatus comprising an enclosed housing having a gas inlet, means for producing a vacuum within the housing, a reactor having an inlet for a reactant gas and an outlet for a product gas, means for introducing a reactant gas into the reactor, means for gas flow communication between the outlet of the reactor and the inlet of the housing, and within the housing, means for providing a real time analysis of product gas exiting the reactor. The reactor has a zone defined therein containing a packed particulate reaction catalyst. The reactor is structured to allow a reactant gas to pass through the packed particles of the catalyst to produce a product gas by slow reaction. The distance between the outlet of the reactor and the real time analysis means is sufficiently short so that high sensitivity analyses may be conducted on reaction product gas exiting the reactor without interference from product gas molecules reflected in the interior surfaces of the housing.

The invention is further directed to an apparatus comprising an enclosed housing having a gas inlet, means for producing a vacuum within the housing, a reactor having an inlet for a reactant gas and an outlet for a product gas, means for introducing a reactant gas into the reactor, means for gas flow communication between the outlet of the reactor and the inlet of the housing, within the housing, means for providing a real time analysis of product gas exiting the reactor, a source of electromagnetic radiation, means for detecting the wavelength and amplitude of the electromagnetic radiation, means in the reactor transparent to electromagnetic radiation and means for directing electromagnetic radiation from the source to the catalyst via the transparent means. The reactor has a reaction zone defined therein containing a packed particulate reaction catalyst and the reactor is constructed to allow a reactant gas to pass through the packed particles of the catalyst to produce a product gas by slow reaction. The apparatus further comprises means for directing electromagnetic radiation reflected from the reaction zone to the means for detecting the wavelength and amplitude of electromagnetic radiation and means for filtering reflected electromagnetic radiation from the reaction zone between the transparent means and the detecting means.

The invention is further directed to a process in which a reactant gas is introduced into a catalytic reaction zone. The gas is passed through the catalytic reaction zone to produce a reaction product gas and the product gas is analyzed in real time using an analysis means that is separated from the outlet of the catalytic reaction zone by a distance sufficiently short so that high sensitivity analyses may be conducted on the reaction product gas.

The invention is further directed to a process in which a reactant gas is introduced into a catalytic reaction zone. The gas is passed through the catalytic reaction zone to produce the reaction product gas and electromagnetic radiation is impinged on the catalytic reaction zone while the gas is passed therethrough. The wavelength and amplitude of electromagnetic radiation reflected from the catalytic reaction zone is detected while the gas is passed through the reaction zone. Simultaneously with the detection of the wavelength and amplitude of the reflected radiation, the product gas is analyzed in real time.

Other objects and features will be in part apparent and in part pointed out hereinafter.

BRIEF DESCRIPTION OF THE DRAWINGS

Corresponding reference characters indicate corresponding parts in the two views of the drawings.

DESCRIPTION OF THE PREFERRED EMBODIMENTS

Figure 1:
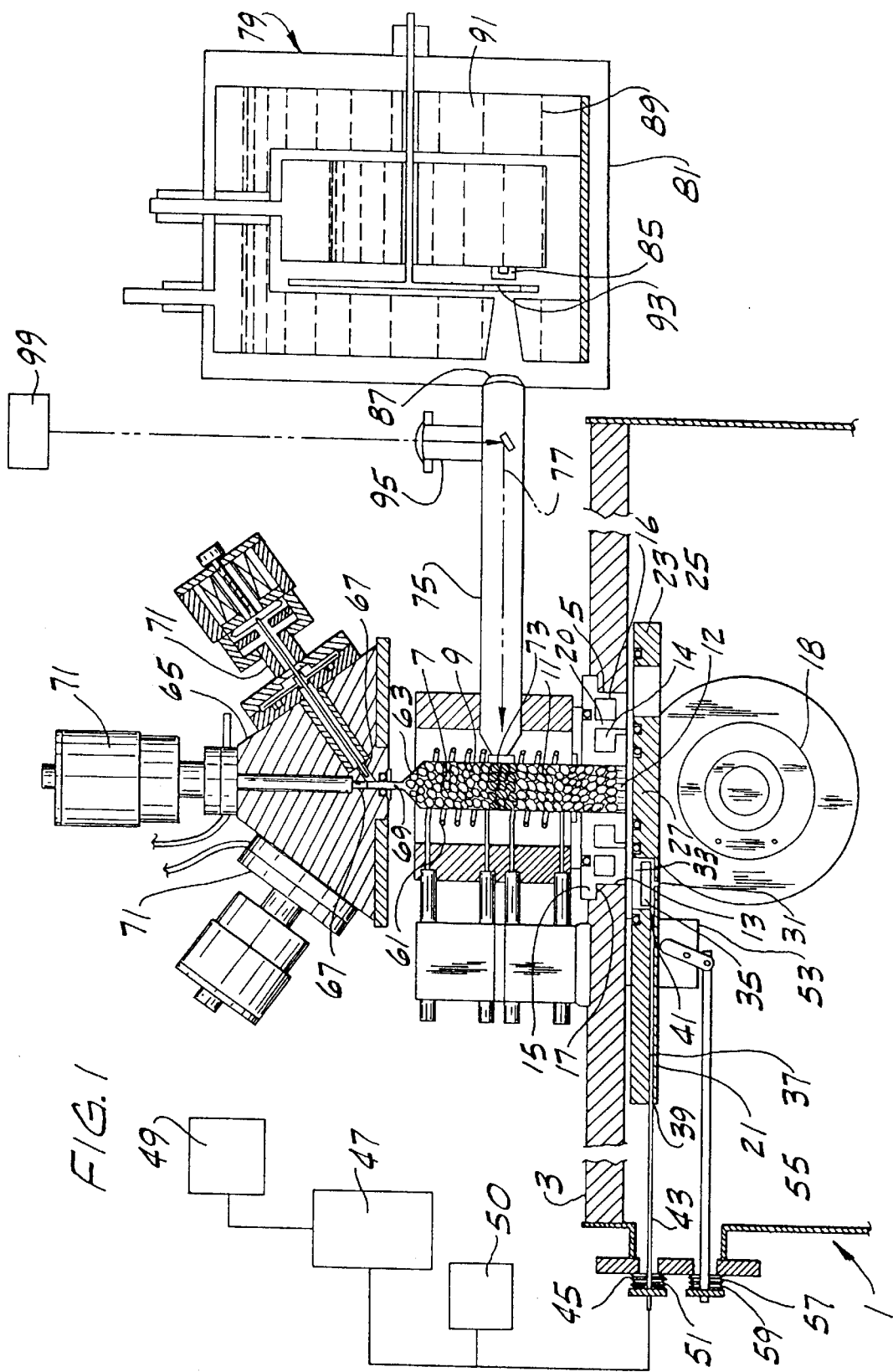
FIG. 1 is a schematic illustration of an apparatus of the invention which may be used for study of catalytic reactions and reaction products.

The apparatus and process of the present invention may be used to study catalytic reactions conducted at high vacuum, ambient pressure or above ambient pressure. Whatever the pressure regime within the reactor, real time analysis of reaction product gases is provided by use of mass spectrometry. Reaction products may also be analyzed by analytical procedures such as gas chromatography or Fourier transform i.r. spectroscopy. Reacting gases, surface intermediates, and the catalyst surface may further be analyzed by infrared or other electromagnetic spectroscopy. By operation of the reactor at pressures comparable to those anticipated in a commercial reactor, the system and apparatus of the invention may be used to simulate commercial reactor operation. In this mode, products of reaction are analyzed by gas chromatography, Fourier transform i.r. spectroscopy or other conventional analytical methods. Simultaneously, a portion of the reaction gas may be bled into the vacuum chamber where a rarified gas comprising a molecular product stream may be analyzed in real time by mass spectroscopy to identify intermediates and provide analytical data from which reaction mechanisms can be determined. Highly transient reaction intermediates can be identified by such real time analyses, whereby mechanisms of reactions can be determined, and competing mechanisms and the kinetics thereof may be evaluated. The process and apparatus are particularly useful in studying unsteady state reaction processes, or in obtaining transient data under unsteady state conditions for evaluation and design of processes that may operate commercially under either steady state or non-steady state conditions.

As in the TAP reactors of the aforesaid patents, a quadrupole for a mass spectrometer or other detecting means for real time analysis of reaction products and intermediates is contained within a high vacuum chamber. Advantageously, a time of flight mass spectrometer may be used instead of a quadrupole for real time analysis. In either case, the reactor is outside the vacuum chamber that contains these detecting means. Though outside the reaction chamber, the reactor outlet for reaction gases is detachably connected to a port of the vacuum chamber so that reaction gases may flow into the chamber. The reactor is also close coupled to the quadrupole or equivalent detecting means so that the reaction products travel a very short distance before capture by the detecting means for real time analysis. By construction of the system to maintain a distance of less than about 1.25 cm between the reactor outlet and the detecting means, it has been found that the sensitivity of the system is enhanced by two or more orders of magnitude as compared to previously available commercial TAPS analytical systems.

A novel valve means interposed between the outlet of the reactor and the inlet of the vacuum chamber provides gas flow communication between the reactor and the vacuum chamber containing the real time detecting means, and thus allows a vacuum established within the vacuum chamber to be extended to the reactor. The valve is also constructed to allow reaction product gas to be directed to a gas chromatograph, either in parallel with the gas flow to the real time detecting means, or in lieu thereof. In the first of these two modes, the valve is closed against flow of gas from the reactor to the interior of the vacuum chamber. In the other of these modes, gas flows to the real time detecting means through a high resistance restriction which allows the vacuum chamber to be maintained at a very low absolute pressure while a relatively elevated pressure, for example, ambient or above, is maintained in the reactor.

FIG. 1 illustrates the apparatus of the invention. Shown at 1 is a totally enclosed vacuum chamber having a cover plate 3. A cylindrical opening 5 in the cover plate provides an inlet for product gas from a reactor 7. Reactor 7 is tubular in configuration and comprises a reaction zone 9 containing a particulate catalyst 11. The lower end of the reactor, comprising a reaction gas outlet 12, extends into opening 5. An annular collar 13 surrounding the reaction gas outlet lower end of reactor 7 fits into opening 5 and has a flange 15 at its upper end which fits into a counterbore 17 in the upper surface of cover plate 3 surrounding opening 5. Counterbore 17 and opening 5 are machined for a secure vacuum tight connection between the annular collar and the cover plate.

Within collar 13 are two concentric annular passages 14 and 16, which are separated by a circular partition 20. A cooling fluid may be passed through passage 16 to cool reaction product gases passing into the vacuum chamber from the reactor. A vacuum may be maintained in passage 14 to insulate the reactor exit from the surroundings.

Within chamber 1 is an ionization cage 18 for a mass spectrometer, and within the ionization cage is a quadrupole detecting means 19 for a mass spectrometer. Quadrupole 19 and ionization cage 18 are close coupled to the outlet of reactor 7 so that gas exiting the reactor travels only a very small distance before capture by the quadrupole. Preferably, the distance is no greater than about 1.25 cm, more preferably between about 0.5 and about 1.0 cm. Between reactor 7 and quadrupole 19 is a slide valve 21 comprising a valve plate 23 which is movable among three different positions along the bottom side of cover plate 3. In one position, an open port 25 in the valve plate is aligned with the exit of reactor 7, providing gas flow communication between the interior of the vacuum chamber 1 and the interior of the reactor. This position provides for free flow of reaction gases, thereby allowing a vacuum established in chamber 1 to be extended to the interior of the reactor 7. In a second position, a solid or otherwise gas impervious segment 27 of the valve plate is aligned with the outlet 12 of the reactor, positively precluding gas flow communication between the interior of the vacuum chamber 1 and the interior of the reactor 7. In the third position, a flow restriction comprising a pin hole 31 at the bottom of a cavity 33 in the cover plate 3 is aligned with the outlet of the reactor, allowing reaction product gas to flow with high pressure drop from the interior of the reactor to the interior of the vacuum chamber. A metal frit 35, positioned in the cavity above the pin hole, prevents dust particles from the reactor from obstructing the pin hole. Valve plate 23 further comprises a lateral bore 37 extending from an opening 39 in the outer periphery of the plate to an opening 41 in the wall of cavity 33. Opening 41 is above pin hole 31 and upstream of the pin hole with respect to product gas flowing from the reactor, but below and downstream of frit 35. A tube 43 extending from opening 39 through an aperture 45 in a side wall of chamber 1 provides gas flow communication between the reactor and both a back pressure regulator 47 and a gas chromatograph 49. Back pressure regulator 47 and chromatograph 49 are arranged in series, with the regulator interposed between the reactor and the chromatograph. A pressure transducer 50 transmits a pressure signal by which the pressure in the reactor may be monitored. Aperture 45 is closed with a bellows 51 which seals the chamber against leakage from the surroundings.

A crank type locking mechanism 53 for the slide valve 21 comprise a metal plate which is movable from a lower position in which it allows free lateral movement of valve plate 23 and an upper position in which it locks against the valve plate, urging the valve plate against the bottom surface of cover plate 3. A locking mechanism 53 includes an operating lever 55 which extends through an aperture 57 in a side wall of chamber 1. Aperture 57 is closed with a bellows 59.

Figure 2:
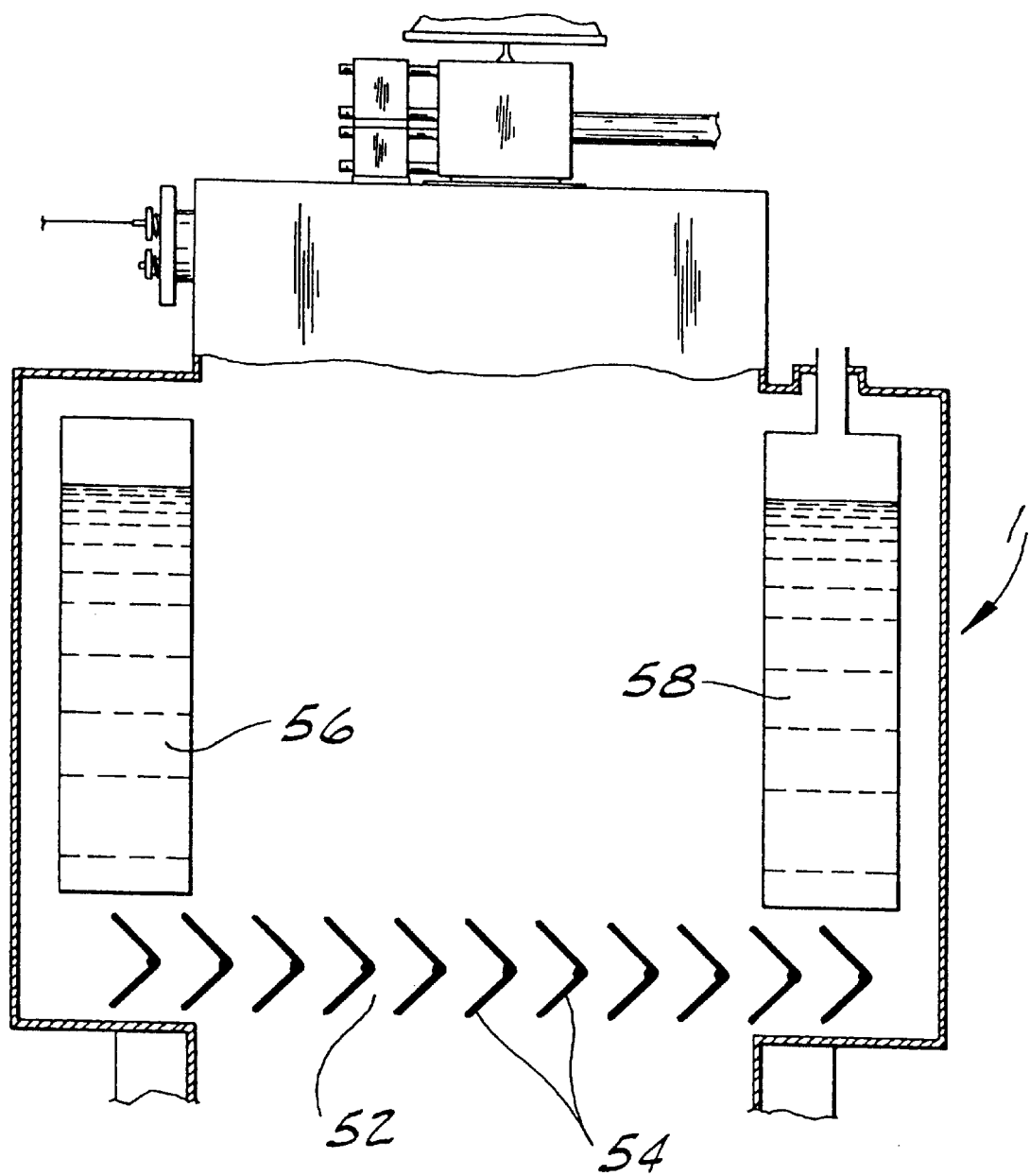
FIG. 2 is an illustration showing further detail of components contained within the vacuum chamber of the apparatus of FIG. 1.

As illustrated in FIG. 2, vacuum chamber 1 contains an adjustable baffle system 52 which comprises a coordinated set of louvers 54 that may be adjusted between a fully open and a fully closed position. Advantageously, a vacuum is drawn in the chamber by use of a diffusion pump. Baffle system 52 is operated to a partially closed position to prevent back streaming of oil from the diffusion pump. A pair of nitrogen dewars 56 and 58 within the vacuum chamber provide a further vacuum pumping for the chamber as well as a cold trap for any backstreaming diffusion pump oil which may flow past baffle system 52.

Reactor 7 is shown as surrounded by an electrical heating coil 61 for supplying heat to the reaction zone. Alternatively, the reactor may be provided with a temperature control system of the type described in U.S. Pat. No. 5,009,849 which provides either heating or cooling to the reaction zone in response to measurement of the temperature therein. The disclosure of U.S. Pat. No. 5,009,849 is expressly incorporated herein by reference. The reactor has an inlet 63 at its upper end which is in gas flow communication with a feed manifold 65. Manifold 65, contains a plurality of inlet channels 67, which are all in gas flow communication with a reactor antechamber 69 immediately adjacent the inlet of the reactor. Each of these channels contains a feed valve at its terminus for admittance of a gas into the mixing chamber antechamber 69 and the reaction zone. One or more of the feed valves, such as that illustrated at 71, are adapted to rapidly operable for introduction of a rapid pulse of a reactant gas into the reactor. Others of the valves may be adapted for continuous feed of reactant or inert gas into the reactor.

In a side wall of reactor 7 is a window 73 that is transparent to infrared radiation. An infrared light pipe 75 having a main conduit 77 that is aligned with window 73 with its axis normal to the axis of the reactor. Light conduit 77 extends between the reactor and an infrared radiation analyzer 79 for measuring the wave length and amplitude of light received by the analyzer. Analyzer 79 comprises a housing 81 having an opening 83 in a side wall thereof in alignment with light conduit 77 and an infrared detector 85 inside the housing that is aligned with both opening 83 and conduit 77. A lens 87 on the light pipe at the opening 83 focuses infrared radiation from the light pipe on the detector 85. Within housing 81 are a liquid nitrogen dewar 89 and a liquid helium dewar 91. A variable band width filter 93 within housing 81 is interposed between lens 87 and detector 85 to block all infrared radiation except that within the band width of the filter.

Light pipe 75 includes a side arm 95 containing a second window 94 positioned in conduit 77 at its junction with side arm 95 and aligned with a tunable infrared radiation source 99. A mirror 101 within the light pipe reflects light from tunable source 99 so that it passes through window 73 and impinges on the reactant gas and catalyst within the reactor. Light reflected from inside the reactor passes back through conduit 77 of the light pipe and through lens 87 and filter 93 to infrared detector 85. By tuning of source 99 to a select frequency and observing the amplitude of reflected light at that frequency as measured by detector 85, infrared analyses can be made of the composition of the reacting gases and the nature of the catalyst surface within the reactor. Although described above with respect to i.r. analysis, the essentially same analytical system may be arranged to operate using electromagnetic radiation outside the i.r. range, e.g., to provide Raman spectroscopy or u.v. analysis of radiation reflected through window 83.

In operation of the apparatus of the drawing in accordance with the process of the invention, a high vacuum is established in vacuum chamber 1; and reactant gases are drawn through valves 71 of manifold 65, mixed in mixing chamber 69 and introduced into reactor 7. Certain reactant gases may be pulsed into the reactor and other reactant or inert gases may be caused to flow continuously therethrough. A variety of flow combinations can be employed as described in further detail hereinbelow. By use of heater 61, or by a combined heating and cooling system of the type described in U.S. Pat. No. 5,009,849, catalytic reaction is carried out at a carefully controlled temperature in reaction zone 9.

Slide valve 21 is operated to cause reaction product gas to flow into vacuum chamber 1, either through unrestricted port 25 or through flow restriction 31 in cavity 33. If operation is desired at a pressure in the reactor that is substantially higher than the low absolute pressure in the vacuum chamber, the slide valve is operated to align flow restriction 31 with the outlet of the reactor. If the reactor is to be operated under high vacuum, port 25 is aligned with the reactor outlet. In the reaction chamber, reactant gases are reacted in the presence of the catalyst, adsorbed thereon or desorbed therefrom. Reaction temperature is controlled by a system of the type disclosed in U.S. Pat. No. 5,009,849. If the reactor is connected to the vacuum chamber via port 25, the vacuum established in the vacuum chamber substantially extends throughout the reaction zone within the reactor. If the reactor is connected to the vacuum chamber via pin hole 3, rather than port 25, pressure in the reactor is controlled by backpressure regulator 47, independently of the pressure in vacuum chamber 1. In high vacuum operational mode, a very low absolute pressure product gas stream flows through port 25 to the capture zone of quadrupole 19 for real time analysis of the products. In higher pressure operation, a fraction of the product gas stream flows through pin hole 31 in cavity 33, and the remainder of the product gas exits the reactor through bore 37 and tube 43 to gas chromatograph 49 and backpressure regulator 47, the latter of which bleeds reaction product gas from the system at a rate sufficient to maintain a desired pressure in the reactor. The fraction of the product gas stream that passes into the reaction chamber via pin hole 31 flows into the capture zone of quadrupole 19 for real time analysis of products.

Regardless of whether the product gas flows through port 25 or pin hole 31, it travels only a very short distance, i.e., preferably less than about 2 cm, more preferably less than about 1.25 cm, most preferably between about 0.1 and about 1.0 cm, before capture by the quadrupole. This enhances the accuracy and sensitivity of the real time analysis of the product gas by allowing capture of a sample of the gas before further reaction or decomposition of intermediate or final reaction products can occur in the reaction product gas exiting the reactor, and before the gas has substantially dispersed after exit from the reactor. Moreover, the volume of the gas stream from which the sample is taken is substantially larger than that of the TAPS apparatus described in U.S. Pat. Nos. 4,626,412, 5,009,049, and 5,039,489. Regardless of the mode of operation, close coupling of the reactor exit with one ionization cage and the quadrupole causes the sample to be taken before the gas has had opportunity for substantial decrease in stream density. As a further consequence, where the reactor is operated in high vacuum mode, a substantial portion of the product gas stream is available for sampling by the quadrupole. In this mode of operation, the only portion of the product gas stream which is not captured by the quadrupole is whatever portion may flow outwardly from the vacuum chamber inlet at an angle so sharp that it escapes the ionization cage. By contrast, in the TAPS apparatus of the aforesaid patents, the product gas must be resolved through a collimating slit before analysis, thereby substantially reducing the fraction of the product gas that is available for sampling. Where the process of the invention is carried out by operating the reactor in pressure mode, only a minor fraction of the gas passes through the pin hole 31 into the vacuum chamber but, because reaction gas is produced at a much larger rate in the reactor, a substantial sample is provided by passage of only a minor fraction of that gas through the pin hole into the quadrupole capture zone. In either case, close coupling allows at least 60%, more commonly at least about 90% of the molecules entering the vacuum chamber to pass through the ionization cage, and thus through the capture zone of the real time detecting means. This is at least two orders of magnitude higher than the proportion of molecules exiting the reactor which fall within the capture zone of the real time detecting means in the systems of the prior art. Thus, the real time analysis provided by the apparatus and process of the invention is at least two orders of magnitude more sensitive than that provided by the aforesaid systems of the prior art, i.e., the molecular concentration within the capture zone of the quadrupole or other real time detecting means is at least $10^2$ to $10^3$ times higher than molecular concentration in the capture zone during operation of the apparatus and process of the prior art. For a given energy input into the ionization cage, the ion concentration, and thus the sensitivity of the analysis is correspondingly higher than in the systems of the prior art.

In the apparatus of the invention, as illustrated in the drawing, the interior of the vacuum chamber is configured to minimize the presence of surfaces from which product gas molecules can be reflected for delayed arrival in the capture zone of the quadrupole. Close coupling of the reactor exit and the quadrupole further helps to prevent contamination of the sample gas with reflected gas molecules. Thus, the combination of close coupling and avoidance of reflecting surfaces is effective to eliminate the need for a collimating slit to produce a resolved product gas stream for analysis by the mass spectrometer.

When the reactor is operated at a pressure substantially higher than the pressure in the vacuum chamber, a side stream passing through bore 37 and tube 43 may be subjected to analysis in gas chromatograph 47. While the chromatograph does not provide a real time analysis effective for the identification of reaction intermediates and study of reaction mechanisms, it provides a measurement of the ultimate composition of the product gas exiting the reactor, and thus allows the reactor to be used for simulation of a commercial scale reactor operating with the feed composition introduced into the reactor. When obtaining data of such nature by use of the chromatograph, the reactor may advantageously be operated in continuous mode. However, simulation may also be conducted by pulsing of one reactant gas combined with continuous flow of another reactant or inert carrier gas. In any case, simultaneously with the measurement of gas composition in the chromatograph, a side stream flowing through pin hole 31 can be subjected to real time analysis by the mass spectrometer, and comparison of this data with the data from the chromatograph may provide further substantial insight regarding the mechanisms of the reaction and the relative effectiveness of different catalysts.

Still further data may be obtained by infrared analysis of reacting gases and catalyst surfaces in the reaction zone by operation of the infrared analyzer. Comparison of this data with that of the mass spectrometer and/or the gas chromatograph may provide a basis for further conclusions on the nature of the reaction and effect of different catalysts.

The apparatus of the invention may be used with a variety of combinations of pulsed and continuous feed of reactant and inert gases. For example, it may be operated to conduct the double pulse and delayed pulse experiments that are described in U.S. Pat. No. 5,009,849. It is especially well adapted for conducting temperature programmed desorption in which a reactant gas is initially passed over the catalyst bed and adsorbed thereon. Thereafter, a carrier gas is flowed continuously through the catalyst zone and the temperature increased according to a programmed schedule. For example, the temperature may be ramped upwardly at a defined heating rate. Analysis of the exit gas by the mass spectrometer provides valuable data on sorptive power of the catalyst for the reactant as a function of temperature.

Similarly, the apparatus and process of the invention may be utilized to conduct temperature programmed reactions. In accordance with this method, a reactant is flowed over a catalyst and the temperature increased or decreased on a controlled schedule. Real time analysis of the products of reaction allow the effect of temperature on reaction rates and mechanisms to be determined. In a particular embodiment of temperature programmed reaction, one reactant may be pre-adsorbed onto the catalyst surface and another reactant caused to flow through the reactor, either in a pulse or continuous flow mode, while the temperature is varied on a programmed schedule. The greatly enhanced sensitivity of the apparatus and process of the invention yield much more useful data from temperature programmed desorption and temperature programmed reaction than has been possible with the TAPS apparatus and method of the aforesaid patents.

Using the apparatus of the invention, a particular catalytic reactor may be operated sequentially at high pressure and then low pressure (or vice versa) without exposing the catalyst to ambient air during conversion from one pressure regime to the other. In fact, this transition can be accomplished while maintaining a constant temperature within the reactor if desired. Thus, for example, carbon or surface intermediates deposited on the catalyst surface during pressure operation may be preserved; and thereafter studied using such techniques as temperature programmed desorption or temperature programmed reaction.

Also, because the reactor is outside of the vacuum chamber, one reactor may be readily removed and another substituted in its place. Reactors of different length and configuration may be used with the same vacuum chamber and feed manifold, the manifold being readily movable up or down to accommodate reactors of different length. Thus, the apparatus of the invention is a modular system in which various reactors of differing configuration can be readily interchanged. The apparatus is equally amenable to modular interchange of manifolds of differing configuration, for example, with different combinations of pulsing and continuous flow valves or different feed temperature control systems.

By comparison of data obtained in operation under high vacuum with operation at commercial reactor pressures, data on surface characteristics of the catalyst and transient reaction intermediates may usefully be correlated with terminal effects under commercial conditions. Moreover, by use of pin hole orifices of different size between the reactor and the vacuum chamber, real time analyses may be obtained over a full spectrum of pressure between commercial operating pressure and very high vacuum. The system is operable to provide data for operation over a pressure range of nine or more orders of magnitude, thereby eliminating the "pressure gap" which had previously plagued the study of catalytic reactions.

What is claimed is:

1. A process for analysis of products of a catalytic chemical reaction comprising providing a reaction zone containing a solid catalyst and having an inlet and an outlet, a real time analysis means in communication with said outlet, and a housing for said real time analysis means, said reaction zone being outside said housing;

introducing a reactant gas into a catalytic reaction zone;

passing the gas through said catalytic reaction zone to produce a reaction product gas; and analyzing the product gas in real time using said real time analysis means, said real time analysis means being separated from the outlet of said catalytic reaction zone by a distance of not more than about 2 cm.

2. A process as set forth in claim 1 wherein said real time analysis means is effective for analysis of products in a capture zone adjacent said analysis means, and said distance between said real time analysis means and said reactor outlet is such that at least about 60% of the molecules of reactant product gas exiting said reactor flow through said capture zone.

3. A process as set forth in claim 2 wherein said analysis means is located in an enclosure under a substantial vacuum, and said reactor is located outside said enclosure, said distance being sufficiently short so that high sensitivity analyses may be conducted on said reaction product without interference from product gas molecules reflected from the interior surfaces of said enclosure.

4. A process as set forth in claim 3 wherein said reactant gas is passed through said catalytic reaction zone at a pressure substantially higher than the pressure in said enclosure, the reaction product gas being divided into two streams, one of the two streams being analyzed in a second analysis means, the other of said streams, constituting a small fraction of said product gas being passed through a flow restriction into said enclosure for analysis by said real time analysis means.

5. A process for analysis of products of a catalytic chemical reaction comprising:

providing a reaction zone containing a solid catalyst and having an inlet and an outlet;

introducing a reactant gas into a catalytic reaction zone;

passing the gas through said catalytic reaction zone to produce a reaction product gas; and analyzing the product gas in real time using an analysis means that is separated from the outlet of said catalytic reaction zone by a distance of less than about 2 cm, thereby providing an analysis of products in the reaction product gas.

6. A process as set forth in claim 5 wherein said distance is less than about 1.25 cm.

7. A process as set forth in claim 5 wherein said distance is between about 0.1 and about 1.0 cm.

* * * * *